United States Patent [19]

Frans

[11] Patent Number: 4,835,708
[45] Date of Patent: May 30, 1989

[54] METHOD AND APPARATUS FOR ANALYSIS OF CHROMATOGRAMS USING CROSS-CORRELATION AND MOMENT ANALYSIS

[75] Inventor: Stephen Frans, San Jose, Calif.

[73] Assignee: Spectra Physics, Inc., San Jose, Calif.

[21] Appl. No.: 69,725

[22] Filed: Jul. 6, 1987

[51] Int. Cl.$^4$ .................... G06F 15/46; G01N 30/02
[52] U.S. Cl. .................................. 364/497; 73/23.1; 364/498
[58] Field of Search .................. 364/497, 498, 604; 73/23.1

[56] References Cited

U.S. PATENT DOCUMENTS

| | | | |
|---|---|---|---|
| 4,169,245 | 9/1979 | Crom et al. | 364/604 |
| 4,180,857 | 12/1979 | Yoshihara et al. | 364/497 |
| 4,524,420 | 6/1985 | Glodo et al. | 364/497 |
| 4,682,027 | 7/1987 | Wells | 364/498 |

OTHER PUBLICATIONS

American Laboratory; vol. 11, No. 2 (Feb. 1979); "Micro-Processor-Controlled HPLC"; R. Fincher et al; pp. 65-76.

T. M. Rossi et al. (1985) Society for Applied Spectroscopy vol. 39, No. 6, pp. 949-959, "Pattern Recognition of Two-Dimensional Fluorescence Data Using Cross--Correlation Analysis".

Primary Examiner—Parshotam S. Lall
Assistant Examiner—Kevin J. Teska
Attorney, Agent, or Firm—Ronald Craig Fish

[57] ABSTRACT

A method and apparatus for comparing substances against other substances or against themselves over time. The method involves taking a chromatogram from each substance and converting each chromatogram to a histogram. The histograms have one bar for each peak on the chromatogram. These histograms are then cross-correlated and the 0th, 1st, 2nd and 3rd moments of the cross-correlation function are calculated. A similarity number in terms of the number of peaks of difference between the two samples compared is then generated by dividing the 3rd moment by the 2nd moment, and the results are displayed. The apparatus of the invention provides the means to gather the data needed for the chromatograms, calculate the histograms, cross-correlation functions and moments and the similarity number and display the result.

10 Claims, 11 Drawing Sheets

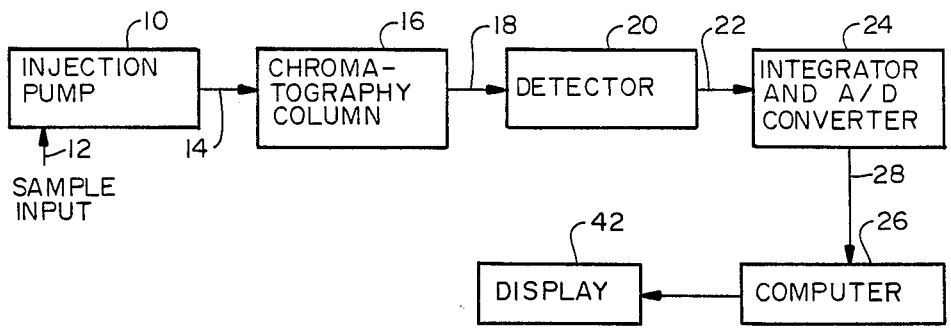
FIG. 1
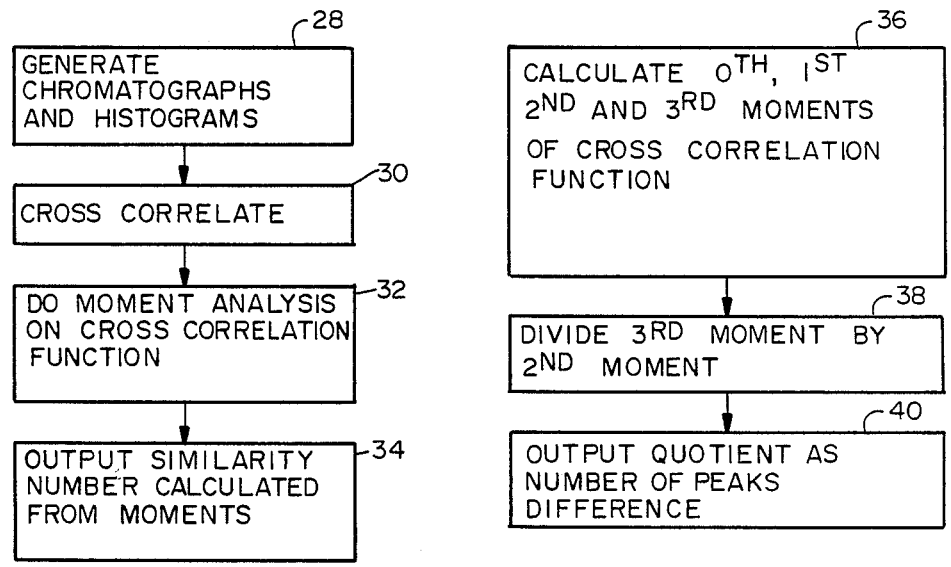
FIG. 2
FIG. 3
$$h(x) = f(x) * g(x) = \int_{-\infty}^{+\infty} f(u-x) g(x) \, du$$
FIG. 4

METHOD AND APPARATUS FOR ANALYSIS OF CHROMATOGRAMS USING CROSS-CORRELATION AND MOMENT ANALYSIS

BACKGROUND OF THE INVENTION

The invention pertains to the field of analysis of chromatograms to determine the identity and composition of the components in liquid and gas compositions. More particularly, the invention relates to the use of known cross-correlation and moment analysis techniques to analyze chromatograms.

It is useful in the chemical analysis arts to be able to identify the individual components in a solution or a gas and the concentration of each component. For example, if groundwater is found to be polluted with gasoline, a chromatogram of the gasoline can be taken and compared to chromatograms of gasoline samples taken from service stations, oil refineries, pipelines and petroleum facilities in the area that could have contributed the pollution. In the past, such analysis was done by hand by injecting the unknown solution into a chromatography column and detecting the various components in the effluent output stream in a known fashion. The detector output was then converted into a chromatogram. Then samples from the known solutions were then injected into the chromatography column and various chromatograms were developed, one for each known solution. Then the chromatogram for the unknown sample is compared to the chromatograms of the known samples by hand to determine the source of the pollution. This has been done in the past by placing the chromatograms one on top of the other on a light table and comparing the chromatograms peak for peak. Obviously, this is a laborious, time consuming and expensive process.

Therefore, a need has arisen for a computerized method and apparatus where chromatograms from various sources can be compared automatically to generate some indication of the degree of similarity or difference.

Cross-correlation analysis is well-known in the arts, and has for many years been used in signal processing. Cross-correlation is a mathematical method of comparing one signal wave form or function to another to determine the degree of similarity. If a high degree of similarity exists, a very large peak will be observed in the cross correlation function at the moment in time when the two waveforms or functions being compared overlap each other to the greatest extent. In the prior art, cross correlation analysis has been used in the field of spectroscopy to compare spectra of excitation-emission matrices. Such a methodology was described in a paper by T. M. Rossi and I. M. Warner entitled "Pattern Recognition of Two-dimensional Florescence Data Using Cross-Correlation Analysis", Volume 39, Number 6, 1985 of Applied Spectroscopy, at page 949. To date however, no cross-correlation analysis has ever been performed by computer on chromatograms.

SUMMARY OF THE INVENTION

According to the teachings of the invention there is provided an apparatus and method for comparing two substances for similarity. The apparatus according to one embodiment of the invention utilizes a pump for injecting two substances into a chromatography column. A detector detects the components in the effluent stream at the output as they appear and generates an analog signal indicative of the concentration of each element in the effluent stream as it appears. This analog signal, if it were plotted, would be a chromatrograph having a plurality of peaks displaced in time, each representing the concentration of one element in the effluent stream. An integrator integrates the analog signal to generate on output signal indicative of the area under each peak in the chromatogram. An analog to digital converter converts the signal from the integrator into a stream of digital data which is read by a ditigtal computer and stored in a file. This digital data is then converted into a histogram, in the preferred embodiment, where the height of each bar on the histogram represents the area under one peak of the chromatogram.

In one embodiment of the invention, histograms are generated in the above manner for each of two samples of unknown composition. In another embodiment the histogram for an unknwon composition can be generated in the above manner and this histogram can be compared to a plurality of histograms previously prepared from a set of known compositions. In still other embodiments either of the above modes of operation are performed on the chromatograms directly without preparing histograms from the chromatograms.

After the pair of histograms or chromatograms are stored in the digital computer, they are used as the two functions for a cross-correlation computation. After the cross-correlation function is calculated, the 0th, 1st, 2nd, and 3rd moments are calculated on the cross-correlation function. These moments define the symmetry and skewness of the cross-correlation function. The ratio of the 3rd moment to the 2nd moment defines the similarity of the two compositions in terms of the difference in the number of peaks in the two chromatograms. This ratio is calculated by the computer and displayed.

BRIEF DESCRIPTION OF THE DRAWINGS

FIG. 1 is a block diagram of a system which is capable of doing cross correlation analysis on chromatograms.

FIG. 2 is a flow chart of the process performed by the embodiment of the invention shown in FIG. 1 in performing a cross correlation and moment analysis on chromatograms.

FIG. 3 is a flow chart of the moment analysis performed in the process shown in FIG. 2.

FIG. 4 is the equation which expresses the mathematical relationship for cross-correlation.

DETAILED DESCRIPTION OF THE PREFERRED EMBODIMENT

Figure 5A:
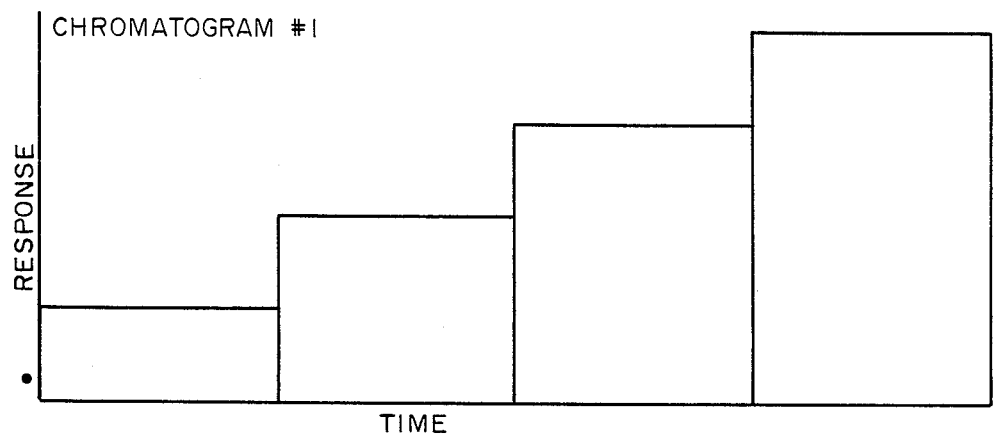
FIGS. 5A–5C illustrate the results of cross-correlating two hypothetical chromatograms.

Referring to FIG. 1 there is shown a block diagram of one embodiment of the invention. The embodiment of FIG. 1 is capable of generating chromatograms and analyzing them using cross-correlation and moment analysis to determine the similarity between two different chromatograms. In other embodiments, a chromatogram may be compared to individual ones of sets of chromatograms each representing one set of known compositions. In these embodiments, a chromatogram from the unknown liquid or gas will be analyzed automatically against each of the chromatograms from the set of known compositions to generate a series of numbers where each number represents the degree of similarity in terms of the number of peaks difference. In other alternative embodiments, the system of FIG. 1 can compare a chromatogram from one unknown sample to the chromatogram of another unknown sample to generate and display a number which is indicative of the similarity between those chromatograms.

The system in FIG. 1 is comprised of an injection pump 10 which receives the unknown sample at a sample imput 12. Injection pump 10 pumps the sample via pipe 14 into a known chromatography column 16. The chromatography column 16 may be either of the liquid or gaseous variety. If it is a gas chromatograph, then the liquid in the pipe 14 is vaporized in the chromatography column 16 and the gas is pushed through the column under pressure. The purpose of the chromatography column 16 is to separate the various components in the input composition in time in the effluent stream 18. This well known process causes the various components in a solution or liquid comprised of multiple components to pass through the column 16 at different speeds. Therefore, the effluent and the output line 18 have different concentrations of the individual components from the input solution at different times.

A detector 20 is used to detect the concentration of each individual component in the effluent stream 18 and generate an output signal on a line 22 which is indicative of the concentration of each individual component in the effluent stream 18 as each component reaches the detector 20.

The output signals on line 22, if plotted, would be a chromatogram with the amplitude of each peak representing the concentration of each element in the effluent stream. The time of occurrence of each peak represents the time each element in the effluent stream reaches the detector 20.

The output signals on line 22 are integrated and converted to digital values by an integrator and analytical digital converter 24. The output digital data stream represents the area under the peaks in the chromatogram. The digital output data stream from the converter 24 is coupled to a computer 26 via a data bus 28. The computer 26 can be any type of computer, either general purpose or special purpose. However, in the preferred embodiment, the computer 26 is an IBM personal computer.

The purpose of computer 26 is to store the incoming digital data on bus 28 as a chromatogram and to do the mathematical analysis to be described below. The computer 26 first converts the chromatogram to a histogram and then does cross-correlation on the histogram from the first sample to a similarly generated histogram from a second sample or from a set of histograms generated from known samples in a similar fashion. After the cross-correlation function generated from the histograms is computed, the computer 26 does a conventional moment analysis on the cross-correlation function calculating the first four moments. The cross-correlation function will, by its shape and skewness, indicate the number of peaks which are different between the two histograms used to generate the cross-correlation function.

The process the computer 26 implements in analyzing the similarity of the substances is given in more detail in FIGS. 2 and 3. These figures are flow charts detailing the process that the overall system performs and detailing of the moment analysis which the computer 26 performs on the cross-correlation function. Referring first to FIG. 2, step 28 symbolizes the process of generating the chromatograms including injection of the various samples into the chromatography column 16 and the detection of the components in effluent stream. This step also symbolizes the process of converting the detector output to digital values. Step 28 can represent either the process of generating two chromatograms injecting two substances into the column 16 or the process of generating one such chromatogram in this manner for the unknown substance and recalling the other chromatogram from memory for a known substance.

Step 30 represents the cross-correlation calculation performed by the computer 26 between the two chromatograms. In the preferred embodiment, the chromatogram from the unknown sample and chromatogram from another unknown sample are both converted to histograms. As is well known in the art, chromatograms consist of a plurality of peaks each of which has an amplitude which represents the concentration of the component represented by that peak in the effluent stream at the particular time or during the particular interval covered by that particular peak. The process of converting the chromatograms to histograms is a process of evaluating the area under each peak in the chromatogram and representing that peak by single bar on a histogram with the height of the bar equal to the area of the peak. Part of this process is performed by block 24. That is the output signal from the detector 20 on line 22 has amplitude which represents the amplitude at any particular time of the signal representing one component in the effluent stream which is then arriving at the detector 20. The integrator in block 24 continually integrates this signal thereby generating an output which is equal to the area under the peak. The analog to digital converter then converts the analog output signals from the integrator to digital values and outputs them on bus 28 to the computer 26. The computer 26, in the preferred embodiment then examines this output digital data stream and converts it to a histogram file where one bar of the histogram represents one peak in the chromatogram. The computer 26 then does the same process for the second chromatogram for the second sample, and then performs a cross-correlation calculation on the two histograms so generated. The cross-correlation function is then stored as a digital file for use by step 32.

Step 32 represents the process performed by the computer 26 in doing conventional moment analysis on the cross-correlation function. The computer 26 does this moment analysis by calculating the first four moments in a known manner. As is well known in the art, the 0th moment defines the area under the cross-correlation function. The 1st moment shows the mean value of the cross-correlation function, while the 2nd moment shows the width of the cross-correlation function. The 3rd moment shows the skewness of the cross-correlation function, or the amount of symmetry in the function. Together these moments define the amount of similarity or dissimilarity between the two histograms which where compared in performing the cross-correlation analysis. From these moments, a number defining this similarity in a single easy to grasp concept can be generated. This process of generating the "similarity number" from the moments is symbolized by block 34 in FIG. 2.

Referring to FIG. 3, there is shown a flow chart of the process which computer 26 follows in performing steps 32 and 34 in FIG. 2. The first step, symbolized by block 36, represents the step of calculating the first four moments. Although the similarity number which ultimately will be derived only requires that the 3rd and 2nd moments be calculated, the 3rd and 2nd moments cannot be calculated until the 0th and 1st moments are calculated. Therefore in step 36, the 0th, 1st, 2nd and 3rd moments are all calculated. Step 38 represents the step of reducing the moments calculated in step 36 to a single number which represents a similarity of the two histograms in terms of the number of peaks difference between the two histograms. In step 38, the 3rd moment is divided by the 2nd moment to derive a single "similarity number" having a dimension equal to the variable used in the cross-correlation function. This number has the dimension of number of peaks or u in the cross-correlation function.

The expression for the cross-correlation function h(x) is as shown in FIG. 4. In this case the function f(x) represents one of the histograms while the function g(x) represents the other histogram. As seen from the integral expression, the cross-correlation function is the sum of the products of the two functions f and g for all values of x with a degree of separation equal to the variable u for all variables u from negative infinity to positive infinity. In other words, the two functions are figuratively passed by each other, multiplied by each other at all overlapping values of x and the products are summed over all u where u represents the amount of separation of the functions. The cross-correlations function is the sum of the products of the two functions at all points of separation where there is some overlap between the two functions. The similarity number calculated in block 38 has the dimension u because the 3rd moment has the dimension $u^3$ while the 2nd moment has the dimension $u^2$. This similarity number is output as symbolized by block 40 to the display 42 in FIG. 1.

Figure 5B:
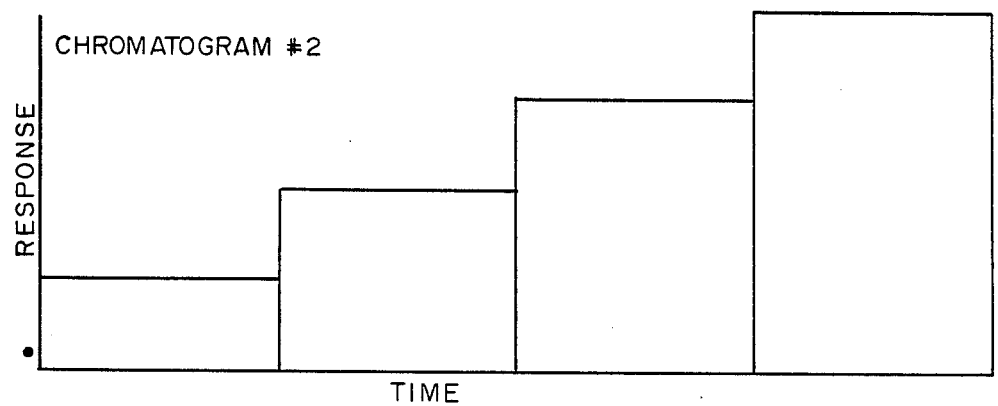
Figure 5C:
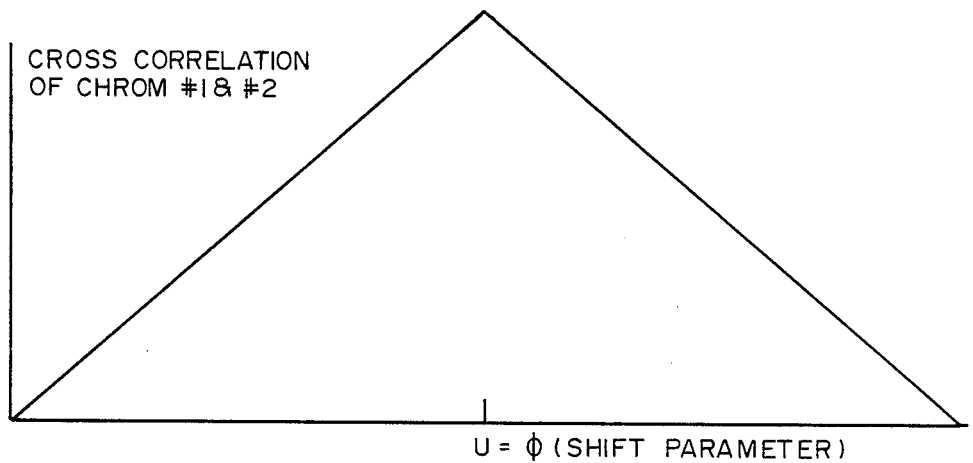

To gain a better understanding of the process disclosed in FIGS. 2 and 3, refer to FIGS. 5A and 5B where two hypothetical chromatograms having an identical number of peaks and identical symmetry are shown. Their cross-correlation function is shown in FIG. 5C. Note that the cross-correlation function in FIG. 5C is symmetrical and has a peak at the point where the chromatograms of FIGS. 5A and 5B exactly coincide.

Figure 6A:
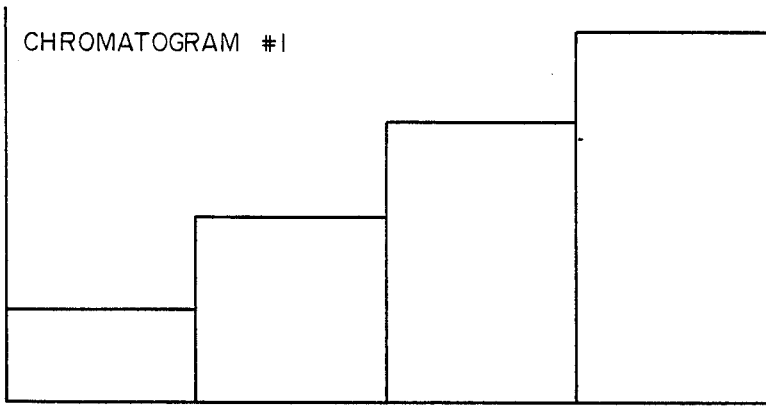
FIGS. 6A–6C illustrate the results of cross-correlating two other hypothetical chromatograms.
Figure 6B:
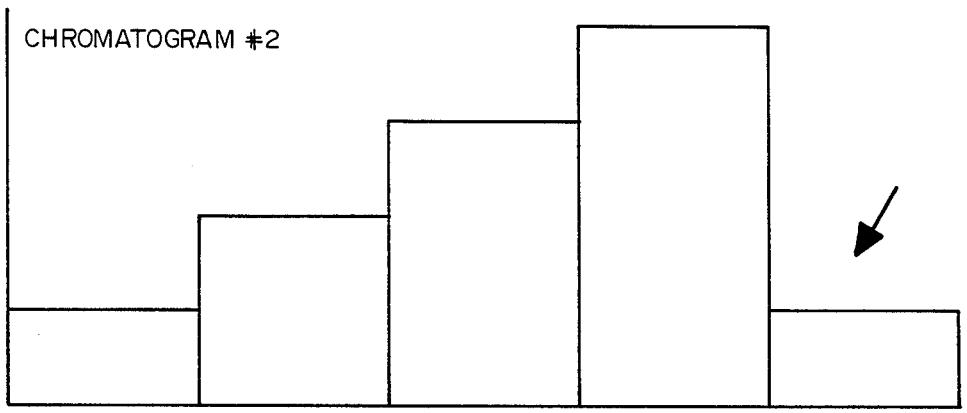
Figure 6C:
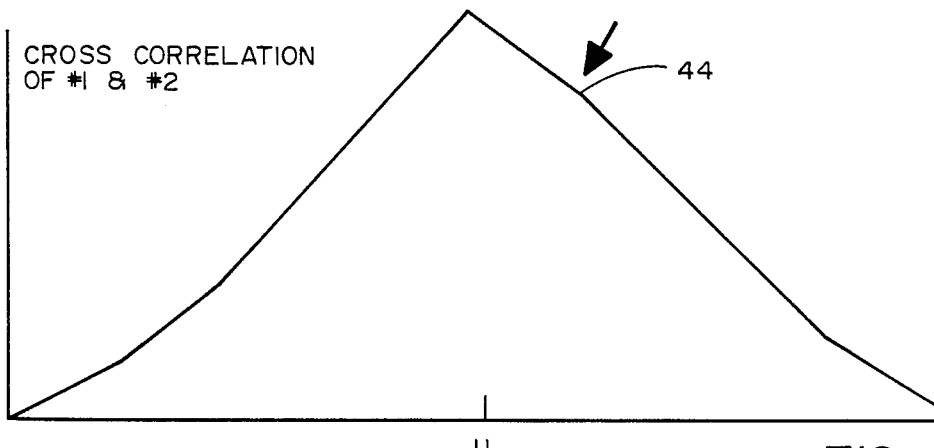

In contrast refer to FIGS. 6A through 6C. In FIG. 6A there is shown a chromatogram which is different from the chromatogram from FIG. 6B and since the chromatogram of FIG. 6A is missing one peak. FIG. 6C shows the cross-correlation function of the histograms of FIGS. 6A and 6B. Note that this cross-correlation function is asymmetrical and has a subpeak at 44 which is caused by the difference of the chromatographs in FIGS. 6A and 6B. This subpeak at 44 would show up in the 3rd moment of the cross-correlation function of FIG. 6C which defines skewness of the cross-correlation function.

Figure 7A:
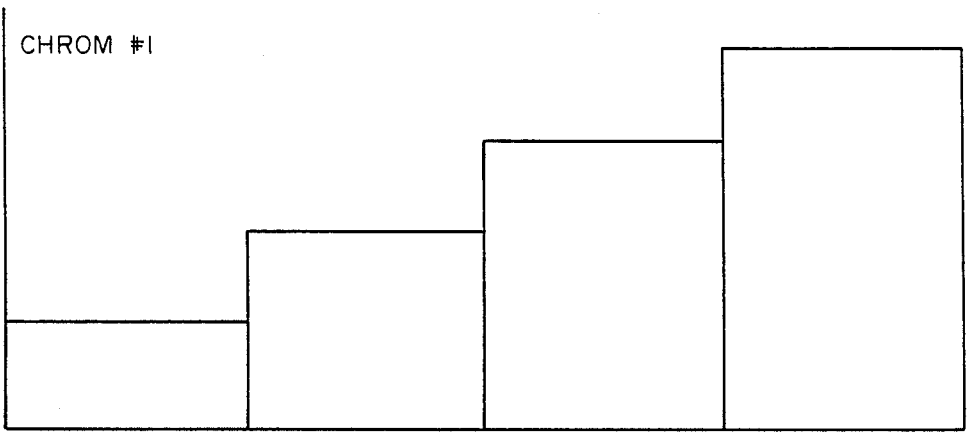
FIGS. 7A–7C illustrate the results of cross-correlating another hypothetical pair of chromatograms.
Figure 7B:
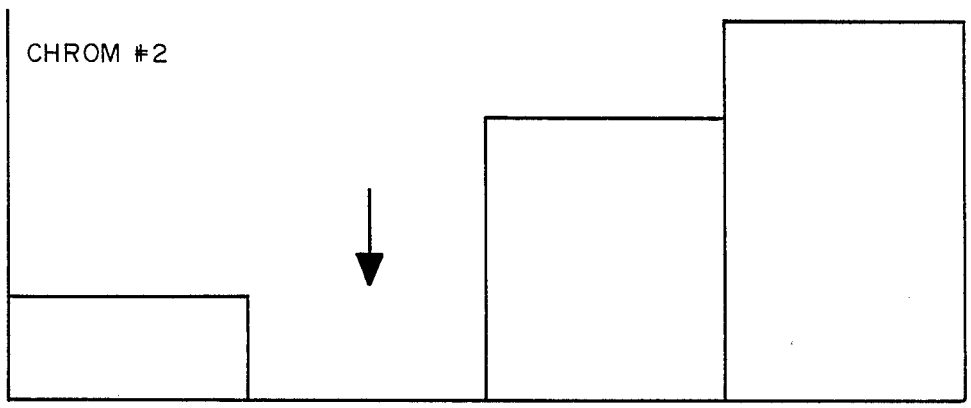
Figure 7C:
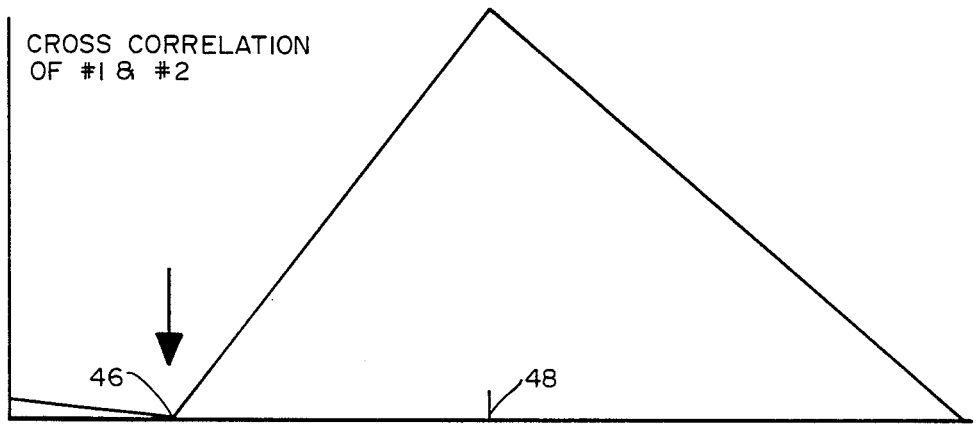

Another example of how differences in numbers and sizes of peaks in chromatograms will cause skewness in the cross-correlation function is in FIGS. 7A through 7C. FIGS. 7A and 7B are chromatograms that differ by one peak. FIG. 7C is the resulting cross-correlation function. This cross-correlation function has a zero at 46, and is asymmetrical about its center point 48.

Thus, it is seen that any difference in the number of peaks between two chromatograms will result in skewness in the resulting cross-correlation function taken between those two chromatograms.

Figure 8A:
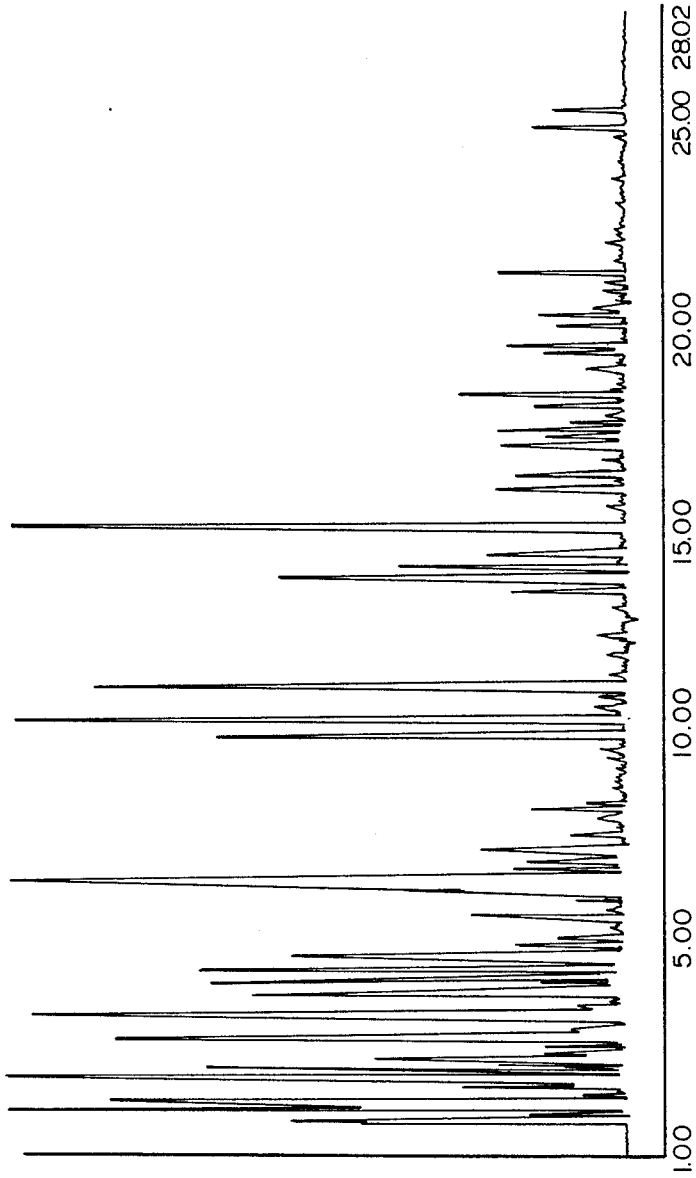
FIG. 8A is an example of an actual chromatogram.
Figure 8B:
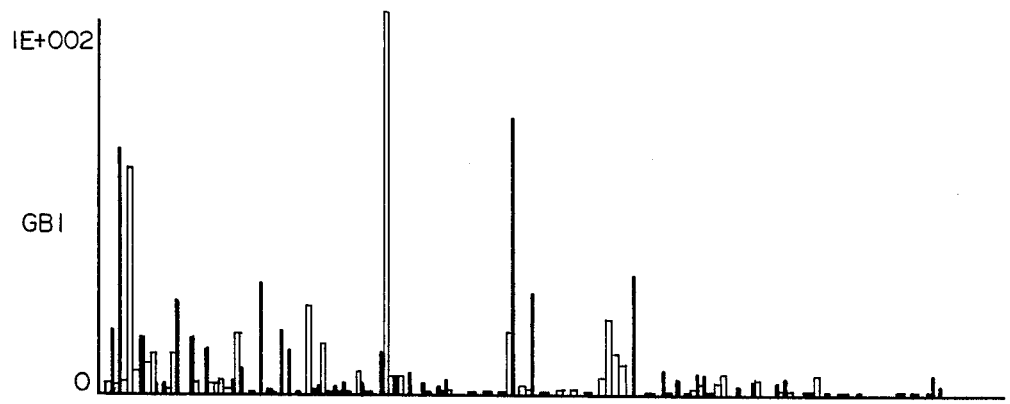
FIG. 8B is a histogram representation of the chromatogram of FIG. 8A where each bar represents a corresponding peak in the chromatogram and has a height which represents the area under the corresponding peak on the chromatogram.

FIG. 8A is an example of an actual chromatogram which can be plotted from the output of the detector on line 22 in FIG. 1. The vertical axis represents the magnitude of the detector output signal, whereas the horizontal axis represents time. FIG. 8B is an example of a histogram prepared from the chromatogram of FIG. 8A by the combination of the integrator and analog to digital converter 24 and the computer 26 in FIG. 1. There is one bar on the histogram for each peak in the chromatogram of FIG. 8A. The vertical axis represents the area under the curve for the corresponding peak. That is, the height of each bar represents the area under the corresponding peak. The horizontal axis in FIG. 8B does not represent time but represents the peak-to-bar correspondence. That is, the first bar on the histogram represents the first peak and the second bar represents the second peak regardless of when that occurs in time.

Figure 9A:
FIGS. 9A–9C represent a typical pair of histograms and the resulting cross-correlation.
Figure 9B:
Figure 9C:

FIGS. 9A–9C represent a typical computation. FIG. 9A and FIG. 9B represent two histograms which have been prepared from two chromatograms from two very similar substances. FIG. 9C represents the cross-correlation function of the histograms of FIGS. 9A and 9B. Note that the cross-correlation function is highly symmetrical with a very large peak at the center. This indicates that the two histograms are extremely similar which in turn indicates that the two substances are extremely similar.

Figure 10A:
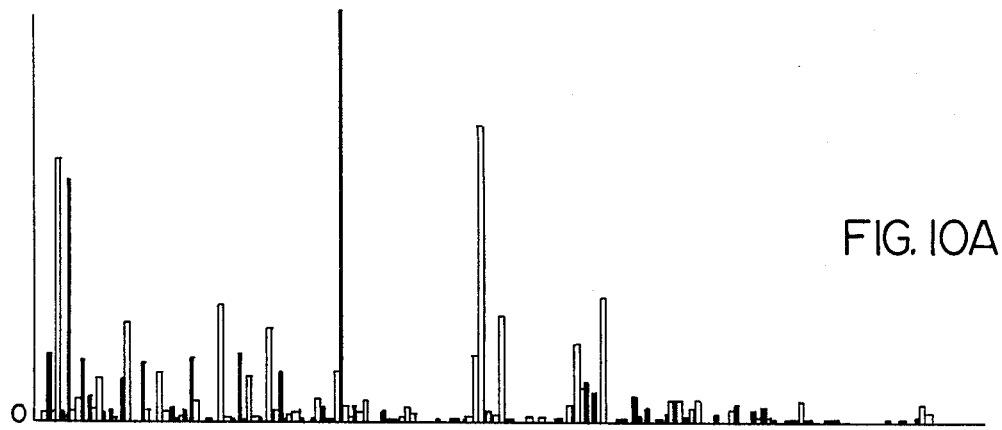
FIGS. 10A–10C represent another pair of histograms and the resulting cross-correlation.
Figure 10B:
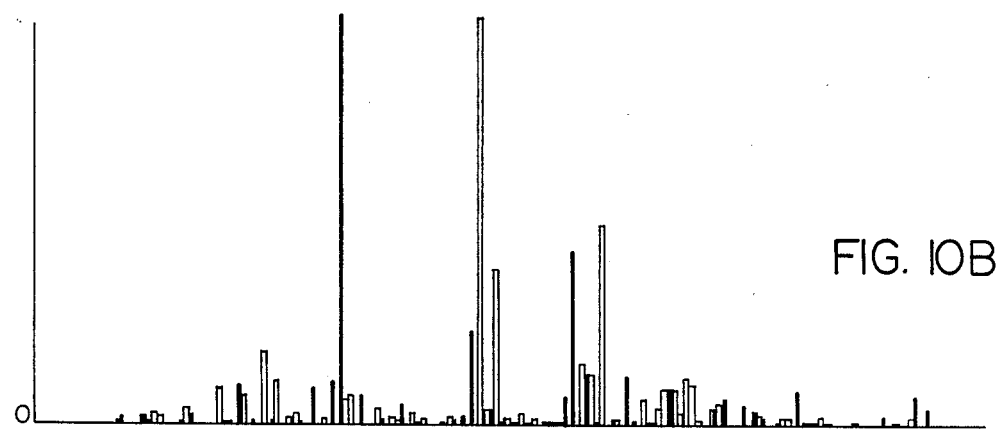
Figure 10C:
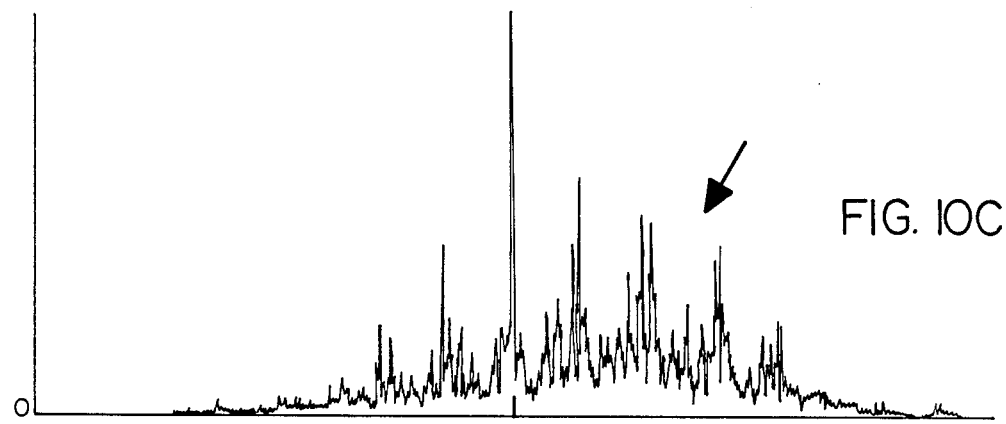

FIGS. 10A–10C represent a typical calculation where the two substances being compared are not as similar as the two substances used to generate FIGS. 9A–9C. FIGS. 10A and 10B represent the histograms prepared from the chromatograms of the two different substances. FIG. 10C represents the resulting cross-correlation function calculated using FIGS. 10A and 10B as the two functions. Note that a cross-correlation function is asymmetrical, and has much higher values on the right side of the central peak than on the left side. The skewness will show up in the 3rd moment of the cross-correlation function.

Figure 11:
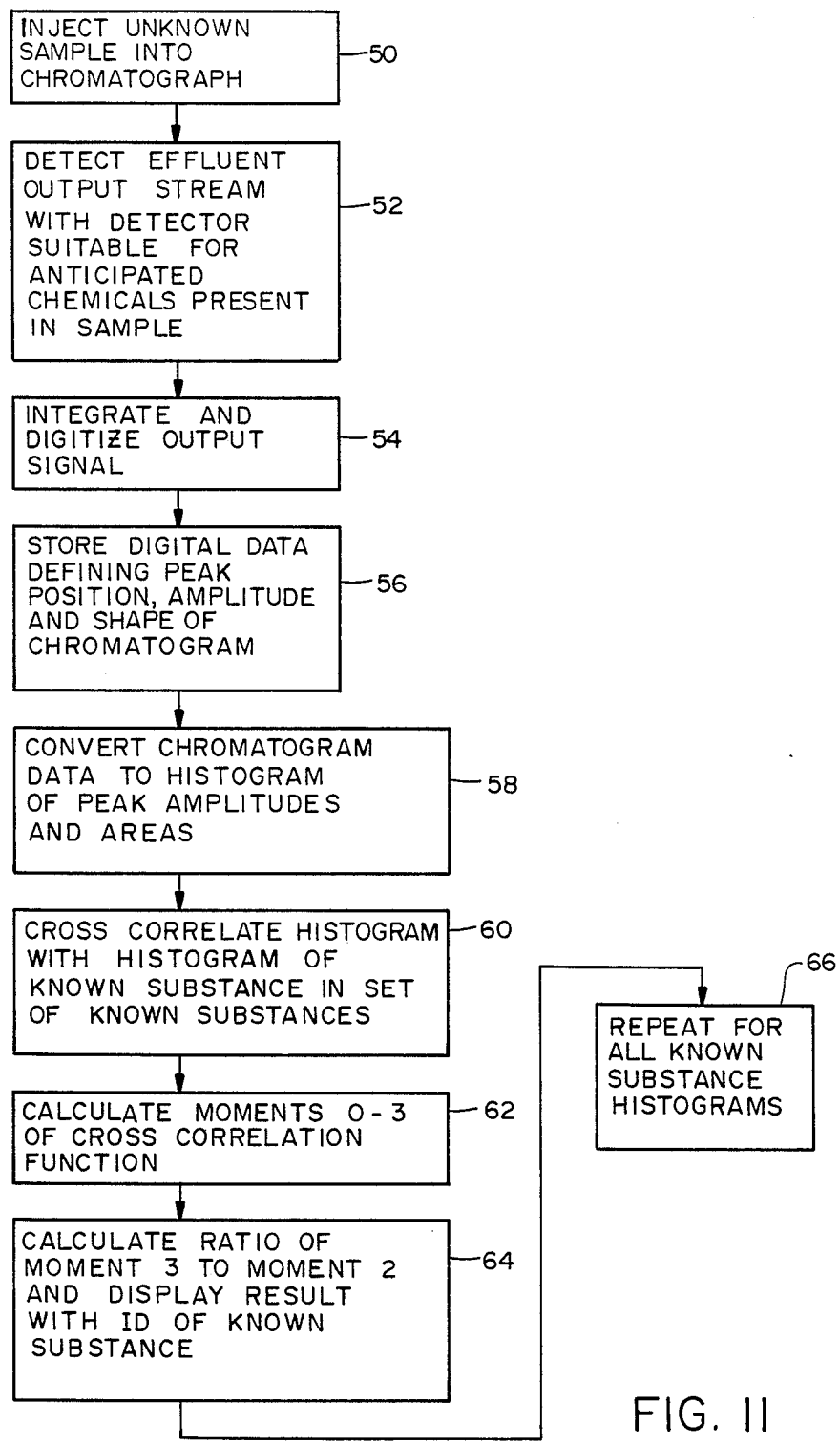
FIG. 11 represent a flow chart of the processing steps to perform the cross-correlation analysis of a sample using the system of FIG. 1 to compare the histogram of the unknown sample to the histograms of a plurality of known substances.

FIG. 11 is a more detailed flow diagram of the system or of the process that the system of FIG. 1 performs.

Block 50 represents the step of pumping a sample of the unknown gas or liquid into the chromatogram 16. Block 52 represents the process of detecting the components in the output stream from the chromatogram with a detector which is suitable for analyzing the anticipated chemical elements which exist in the input solution. Block 54 represents the operation of the integrator in analog-to-digital converter 24 in integrating and digitizing the output signal from the detector in line 22. Block 56 represents the process of storing the digital data on bus 28 from the output of the analog-to-digital converter. This digital data defines the peak positions, amplitude, and shape of the chromatogram in general.

Block 58 represents the process performed by the digital computer of converting the chromatogram data to a histogram like that shown in FIG. 8B.

In the embodiment of FIG. 11, the histogram of the unknown sample is compared with the histograms of a plurality of known substances whose histograms have been previously prepared and stored in the digital computer. Step 60 in FIG. 11 therefore represents the cross-correlation calculation of the histogram generated in step 58 with one of the histograms from the set of known substances.

Steps 62 and 64 represent the calculation of the first four moments of the cross-correlation function calculated in step 60 and the calculation of the ratio of the 3rd moment to the 2nd moment and a display of this ratio on the output display 42 along with identification information of the known substance to which the second histogram used in the cross-correlation function corresponds. Step 66 represents the repetition of steps 60, 62 and 64 for all of the other histograms for the known substances.

Figure 12:
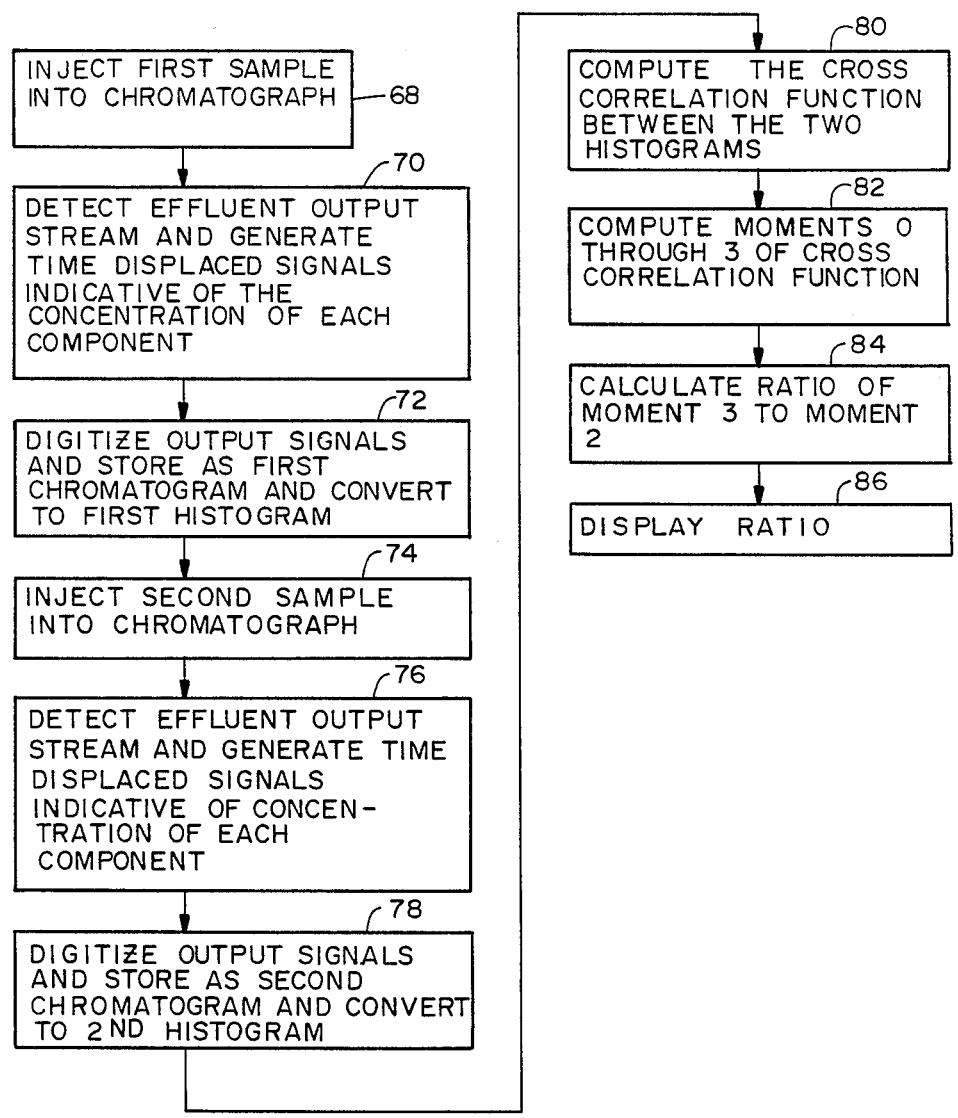
FIG. 12 is a flow chart of the process steps for a cross-correlation analysis of the histograms of two different samples against each other.

FIG. 12 represents the process performed by the system of FIG. 1 in an embodiment where two unknown samples are compared against each other. In this embodiment, the first sample is injected into the chromatograph as symbolized by step 68 and the data resulting therefrom is converted into a first chromatogram and then into a first histogram symbolized by steps 70 and 72. Steps 74, 76 and 78 represent the process of injecting the second unknown sample into the chromatograph and generating a second histogram from the data resulting therefrom.

Steps 80 and 82 represent the computation of the cross-correlation function between the two histograms in the computation of the first four moments of the cross-correlation function. Finally, in steps 84 and 86 the ratio of the 3rd moment to the 2nd moment is calculated and displayed.

Figure 13:
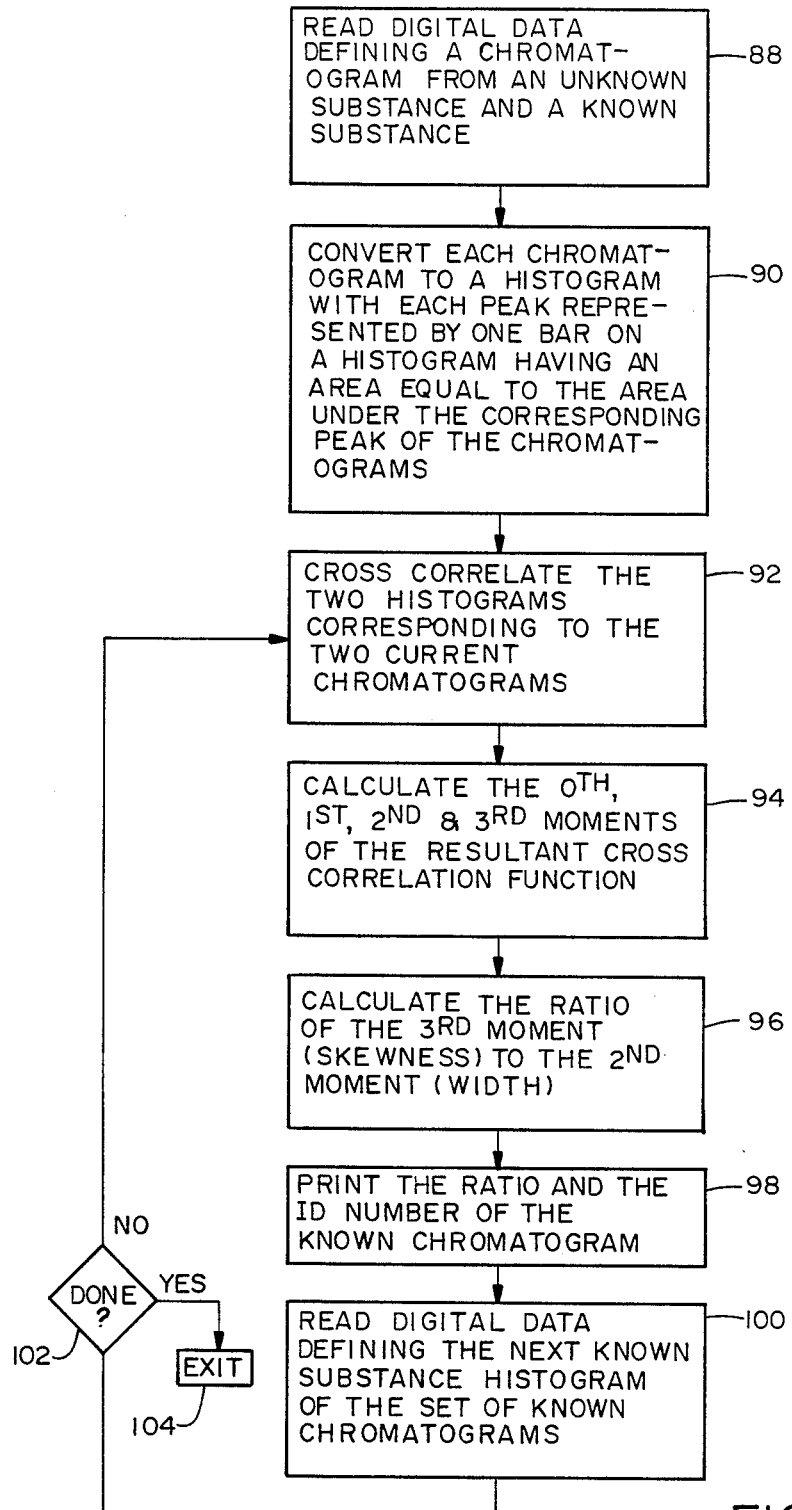
FIG. 13 is a flow chart of the process steps for cross-correlation and moment analysis comparison between the histograms of an unknown substance and a known substance.

FIG. 13 represents a more detailed flow diagram of the procedure that the computer 26 follows in the case of comparing a chromatogram from an unknown substance to the chromatograms of a series of known substances which have been previously prepared and stored in the computer. Step 88 represents the process of reading in the digital data which defines the chromatogram from the unknown substance, and the process of reading in the chromatogram data from the known substance. Step 90 represents the process of converting each of these two chromatograms to a histogram. The histograms are prepared such that each peak in the chromatogram is represented by one peak on the corresponding histogram. The bar on the corresponding histogram has an area equal to the area under the corresponding peak of the corresponding chromatogram. Step 92 represents the process of computing the cross-correlation function of the two histograms which correspond to the two current chromatograms. Step 94 represents the process of calculating the 0th, 1st, 2nd and 3rd moments of the resulting cross-correlation function. Step 96 represents the calculation of the ratio of the 3rd moment defining the skewness of the resulting cross-correlation function to the 2nd moment which defines the width of the cross-correlation function. Step 98 represents the output of the result in the form of printing the ratio calculated in step 96 along with the identification number of the known chromatogram which was used in the calculation.

Step 100 symbolizes the process of reading in the digital data for the next known substance chromatogram from the set of known chromatograms. Step 102 represents a test to determine if the previous chromatogram was the last chromatogram in the set of known chromatograms. If the answer is "yes" the program is exited as symbolized by block 104. If the answer is "no" processing proceeds back to block 92 to calculate the cross-correlation function of the histogram from the unknown substance to the new histogram taken from the set of known histograms which are stored in the computer.

Figure 14:
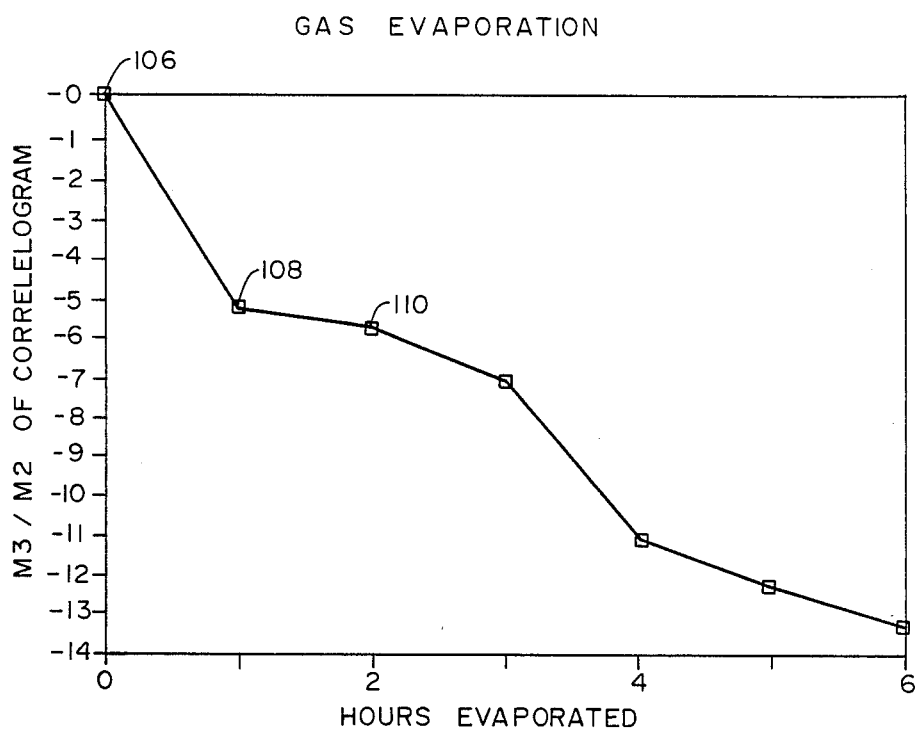
FIG. 14 is a plot of the output similarity numbers generated using the analysis process of the invention on gasoline.

FIG. 14 represents a plot of the output similarity numbers generated using the process defined herein on gasoline. Each point represents one comparison between a sample of the gasoline at time zero and another sample of the gasoline taken after a certain amount of time has been allowed to pass and certain component members of the gasoline have evaporated. The first point at 106 represents two samples taken at the same time. The second point at 108 represents the sample taken at time zero compared to the sample taken one hour later. The point at 110 represents the comparison between the sample taken at time zero and the sample taken two hours later. The vertical axis represents the similarity number which resulted from the calculation, and the horizontal axis represents the time span between the two samples. As can be seen from FIG. 14, as time between the two samples became larger, the number of peaks difference of the chromatograms as represented by the ratio m3/m2 of the "correlogram" (another term for the cross-correlation function) becomes larger.

Appendix A, attached, is an object code listing of the program run by computer 26 according to the teachings of the invention.

Although the invention has been described in terms of the preferred and alternative embodiments disclosed herein, those skilled in the art will appreciate many modifications which can be made to the above-disclosed apparatus and process. All such modifications are intended to be included within the scope of the claims appended hereto.

APPENDIX A

IBM PC Object Code Listing
DUMP OF CORRE. EXE

FILE SIZE = A2H 512 BYTE PAGES, 110H BYTES IN LAST PAGE
OF BASE FIXUPS = 763.
HEADER SIZE IS E00H
FREE MEMORY NEEDED = B040H
HIGH/LOW SWITCH = FFFF0H
STACK ADDRESS IS 1355:E000
CHECKSUM IS B0F3H
STARTING ADDRESS IS 291:60C
FIXUP TABLE @ 1C:

| | | | | | | | | | | | |
|---|---|---|---|---|---|---|---|---|---|---|---|
| 0: | 6C | 0: | 5F | 0: | 57 | 0: | 4E | 0: | 31 | 0: | 1F |
| 0: | 10 | 0: | 9 | 1346: | 2 | 0: | 97 | 0: | 88 | 0: | 82 |
| 0: | DF | 0: | CD | 0: | BB | 0: | AE | 0: | 11A | 0: | 10D |
| 0: | 105 | 0: | FC | 1346: | 4 | 0: | 166 | 0: | 15C | 0: | 145 |
| 0: | 139 | 0: | 130 | 0: | 17E | 0: | 176 | 1346: | 6 | 0: | 194 |
| 0: | 18C | 1346: | S | 0: | 185 | 0: | 1AD | 0: | 1A4 | 1346: | A |
| 0: | 1F6 | 0: | 1EE | 0: | 1E5 | 0: | 1DE | 0: | 1D6 | 0: | 1CE |
| 0: | 1C5 | 1346: | C | 0: | 23B | 0: | 231 | 0: | 229 | 0: | 221 |
| 0: | 21B | 0: | 213 | 0: | 206 | 0: | 26A | 0: | 254 | 0: | 243 |
| 1346: | E | 0: | 2AD | 0: | 299 | 0: | 2BB | 1346: | 10 | 0: | 2FC |
| 0: | 2D0 | 0: | 37A | 0: | 367 | 0: | 354 | 0: | 340 | 1346: | 12 |
| 0: | 3E7 | 0: | 3AE | 1346: | 14 | 0: | 408 | 0: | 401 | 0: | 3F9 |
| 1346: | 16 | 0: | 45D | 0: | 455 | 0: | 448 | 0: | 441 | 0: | 439 |
| 0: | 424 | 0: | 41F | 0: | 49E | 0: | 491 | 0: | 478 | 1346: | 18 |
| 0: | 509 | 0: | 501 | 0: | 545 | 0: | 52F | 0: | 515 | 0: | 575 |
| 0: | 560 | 0: | 613 | 0: | 5DE | 0: | 5D8 | 0: | SCF | 0: | 58D |
| 0: | 689 | 0: | 665 | 0: | 638 | 0: | 6C8 | 0: | 78A | 0: | 783 |
| 0: | 76A | 0: | 755 | 0: | 750 | 0: | 747 | 0: | 727 | 0: | 7BC |
| 0: | 7AB | 0: | 79B | 1346: | 1E | 0: | 7F7 | 1346: | 20 | 0: | 80F |
| 0: | 50A | 1346: | 22 | 1346: | 24 | 0: | 850 | 0: | 89D | 0: | 89B |
| 0: | 88E | 0: | 889 | 0: | 87F | 0: | 86C | 0: | 859 | 1346: | 2E |
| 1346: | 30 | 0: | BEC | 0: | 8D8 | 0: | 989 | 0: | 9B4 | 0: | 97A |
| 0: | 975 | 0: | 968 | 0: | 953 | 0: | 945 | 0: | 93C | 0: | 9D8 |
| 0: | 9C4 | 0: | A58 | 0: | A44 | 0: | AD7 | 0: | AC3 | 0: | C08 |
| 0: | C06 | 0: | 8FE | 0: | 8CC | 0: | BC7 | 0: | 88F | 0: | 892 |
| 0: | BBA | 0: | BB2 | 0: | B75 | 0: | B6D | 0: | B5A | 0: | B50 |
| 0: | B46 | 0: | B33 | 0: | B29 | 0: | C45 | 0: | C3F | 0: | C36 |
| 0: | CE6 | 0: | CD6 | 0: | CBF | 0: | CBB | 0: | CA3 | 0: | C9B |
| 0: | C94 | 0: | C7F | 0: | C5D | 0: | C57 | 0: | C4E | 0: | D23 |
| 0: | D18 | 0: | D05 | 1346: | 36 | 1346: | 38 | 1346: | 3A | 1346: | 3C |
| 1346: | 3E | 0: | E81 | 0: | EA0 | 0: | E7A | 0: | E72 | 0: | E68 |
| 1346: | 40 | 0: | F60 | 0: | F55 | 0: | F0B | 0: | EFD | 0: | FFB |
| 0: | FE4 | 0: | FD9 | 0: | 1096 | 0: | 1031 | 0: | 100E | 0: | 1123 |
| 0: | 10DD | 0: | 11E4 | 0: | 118D | 0: | 1186 | 0: | 1170 | 0: | 1169 |
| 0: | 1248 | 0: | 1234 | 0: | 121A | 0: | 1200 | 0: | 133E | 0: | 1339 |
| 0: | 132F | 0: | 1327 | 0: | 131D | 0: | 130F | 0: | 1305 | 0: | 12FB |
| 0: | 12F3 | 0: | 12E9 | 0: | 1289 | 0: | 1284 | 0: | 12AC | 0: | 1272 |
| 0: | 126A | 0: | 125E | 0: | 1351 | 0: | 1349 | 0: | 13BC | 0: | 13B4 |
| 0: | 1399 | 0: | 1391 | 0: | 13BC | 0: | 1384 | 0: | 137C | 0: | 135F |
| 0: | 135A | 0: | 14DC | 0: | 14D7 | 0: | 14D2 | 0: | 14B6 | 0: | 14B1 |
| 0: | 14A3 | 0: | 148E | 0: | 1489 | 0: | 1481 | 0: | 1479 | 0: | 1465 |
| 0: | 1460 | 0: | 145B | 0: | 143F | 0: | 143A | 0: | 142F | 0: | 13EA |
| 0: | 13E2 | 0: | 13DD | 0: | 13CS | 0: | 162E | 0: | 1619 | 0: | 1604 |
| 0: | 1582 | 0: | 1557 | 0: | 1552 | 0: | 154D | 0: | 1531 | 0: | 152C |
| 0: | 151E | 0: | 1509 | 0: | 1504 | 0: | 14FC | 0: | 14F4 | 0: | 1683 |
| 0: | 16AB | 0: | 16A1 | 0: | 167D | 0: | 1667 | 0: | 1653 | 0: | 1647 |
| 0: | 1636 | 0: | 16E0 | 0: | 16DB | 0: | 16D0 | 0: | 16C6 | 0: | 16FB |
| 0: | 16EE | 0: | 16E9 | 0: | 1739 | 0: | 1728 | 0: | 1709 | 0: | 1704 |
| 0: | 191F | 0: | 18F7 | 0: | 18EA | 0: | 18C7 | 0: | 18A5 | 0: | 18A0 |
| 0: | 17FC | 0: | 17DC | 0: | 17B4 | 0: | 17A7 | 0: | 17B4 | 0: | 1762 |
| 0: | 175D | 0: | 1754 | 0: | 1747 | 0: | 1742 | 0: | 198F | 0: | 1983 |
| 0: | 1979 | 0: | 1972 | 0: | 195E | 0: | 1942 | 0: | 1A3E | 0: | 1A39 |
| 0: | 1A34 | 0: | 1A2C | 0: | 1A21 | 0: | 1ACA | 0: | 1A86 | 0: | 1AA6 |
| 0: | 1A9E | 0: | 1A95 | 0: | 1A85 | 0: | 1A7D | 0: | 1A74 | 0: | 1A64 |
| 0: | 1A5C | 0: | 1A54 | 0: | 1A43 | 0: | 1AD7 | 0: | 1B76 | 0: | 1C02 |
| 0: | 1CBE | 0: | 1D6A | 0: | 1D65 | 0: | 1D5D | 0: | 1D32 | 0: | 1D2D |
| 0: | 1D25 | 0: | 1CF9 | 0: | 1CF1 | 0: | 1CE9 | 0: | 1CDC | 0: | 1CC6 |
| 0: | 1F5F | 0: | 1F5A | 0: | 1F52 | 0: | 1F4D | 0: | 1F43 | 0: | 1F3E |
| 0: | 1F34 | 0: | 1F2C | 0: | 1F14 | 0: | 1F0F | 0: | 1F0A | 0: | 1EEE |
| 0: | 1EE9 | 0: | 1EDE | 0: | 1EB5 | 0: | 1EB0 | 0: | 1EA7 | 0: | 1E9F |
| 0: | 1E97 | 0: | 1E92 | 0: | 1E76 | 0: | 1E60 | 0: | 1E65 | 0: | 1E4A |
| 0: | 1E42 | 0: | 1E3D | 0: | 1E35 | 0: | 1E20 | 0: | 1E10 | 0: | 1E08 |
| 0: | 1E02 | 0: | 1DFA | 0: | 1DEF | 0: | 1DEA | 0: | 1DE0 | 0: | 1DD8 |
| 0: | 1DCE | 0: | 1DC0 | 0: | 1DB6 | 0: | 1DAC | 0: | 1DA4 | 0: | 1D9A |
| 0: | 201A | 0: | 1FF9 | 0: | 1FF4 | 0: | 1FEC | 0: | 1FE4 | 0: | 1FCC |
| 0: | 1FC7 | 0: | 1FC2 | 0: | 1FA6 | 0: | 1FA1 | 0: | 1F96 | 0: | 20B9 |
| 0: | 21E9 | 0: | 21E1 | 0: | 21D9 | 0: | 21D0 | 0: | 21CB | 0: | 21BF |
| 0: | 2189 | 0: | 2180 | 0: | 21A5 | 0: | 219F | 0: | 2196 | 0: | 2191 |
| 0: | 2183 | 0: | 2173 | 0: | 216D | 0: | 2164 | 0: | 2138 | 0: | 2130 |
| 0: | 2128 | 0: | 211F | 0: | 2117 | 0: | 2108 | 0: | 2105 | 0: | 20FC |
| 0: | 20F2 | 0: | 20ED | 0: | 20E3 | 0: | 20D3 | 0: | 20AC | 0: | 20A4 |

APPENDIX A-continued

IBM PC Object Code Listing
DUMP OF CORRE. EXE

FILE SIZE = A2H 512 BYTE PAGES, 110H BYTES IN LAST PAGE
OF BASE FIXUPS = 763.
HEADER SIZE IS E00H
FREE MEMORY NEEDED = B040H
HIGH/LOW SWITCH = FFFF0H
STACK ADDRESS IS 1355:E000
CHECKSUM IS B0F3H
STARTING ADDRESS IS 291:60C
FIXUP TABLE @ 1C:

| | | | | | | | | | | | |
|---|---|---|---|---|---|---|---|---|---|---|---|
| 0: | 2095 | 0: | 23A5 | 0: | 2396 | 0: | 238C | 0: | 237C | 0: | 2358 |
| 0: | 2355 | 0: | 234C | 0: | 2344 | 0: | 233E | 0: | 2335 | 0: | 232D |
| 0: | 2327 | 0: | 231E | 0: | 2303 | 0: | 22FD | 0: | 22F4 | 0: | 22EF |
| 0: | 22E6 | 0: | 22E1 | 0: | 22D4 | 0: | 22CC | 0: | 22C7 | 0: | 228E |
| 0: | 2289 | 0: | 22AE | 0: | 22A6 | 0: | 22A1 | 0: | 2298 | 0: | 2293 |
| 0: | 2288 | 0: | 2280 | 0: | 2270 | 0: | 226A | 0: | 2261 | 0: | 225C |
| 0: | 2253 | 0: | 224E | 0: | 2243 | 0: | 223B | 0: | 2236 | 0: | 2220 |
| 0: | 2228 | 0: | 221D | 0: | 2215 | 0: | 24S3 | 0: | 2474 | 0: | 246A |
| 0: | 2451 | 0: | 243D | 0: | 240F | 0: | 23FB | 0: | 23EC | 0: | 23E2 |
| 0: | 23B9 | 0: | 2569 | 0: | 2555 | 0: | 2546 | 0: | 253C | 0: | 2523 |
| 0: | 250F | 0: | 2500 | 0: | 24F6 | 0: | 24DD | 0: | 24C9 | 0: | 24BA |
| 0: | 24B0 | 0: | 2497 | 0: | 25B5 | 0: | 25AD | 0: | 25BC | 0: | 25B4 |
| 1346: | 74 | 1346: | 72 | 1346: | 70 | 1346: | 6E | 1346: | 6C | 1346 | 6A |
| 25B: | 1BA | 25B: | 183 | 25B: | 16B | 25B: | 15D | 25B: | 156 | 25B: | 13B |
| 258: | CF | 25B | CS | 258: | 5F | 258: | 51 | 258: | 43 | 258: | 35 |
| 258: | 27 | 258: | 15 | 1346: | 76 | 258: | 361 | 258: | 359 | 258: | 340 |
| 25B: | 303 | 25B: | 2F4 | 25B: | 2C2 | 25B: | 2B3 | 25B: | 2AC | 25B: | 294 |
| 25B: | 2B6 | 25B: | 27F | 25B: | 234 | 25B: | 22D | 25B: | 211 | 25B: | 1FF |
| 25B: | 1F8 | 25B: | 157 | 25B: | 199 | 291: | 145 | 1345: | 8 | 1345: | C |
| 1345: | 10 | 1346: | 78 | 40D: | 49A | 40D: | 4B5 | 40D: | 469 | 40D: | 44D |
| 40D: | 41E | 40D: | 405 | 40D: | 3CD | 40D: | 39A | 40D: | 385 | 40D: | 346 |
| 40D: | 31S | 40D: | 2DD | 40D: | 2AD | 40D: | 1F9 | 40D: | 1A7 | 40D: | 169 |
| 40D: | 126 | 40D: | 104 | 40D: | E1 | 40D: | 485 | 291: | 27F | 12D6: | 32E |
| 291: | 60D | 291: | 6ED | 291: | 709 | 291: | 70E | 291: | 733 | 291: | 73A |
| 291: | 740 | 291: | 79A | 1346: | 82 | 458: | 155 | 458: | 131 | 458: | 103 |
| 458: | CF | 458: | 6F | 472: | 8D | 472: | 56 | 1346: | 84 | 291: | 786 |
| 291: | 7C7 | 291: | 813 | 47D: | 32 | 47D: | 13 | 481: | 47 | 481: | 35 |
| 481: | 1A | 481: | F | 486: | 5F | 486: | 3F | 4BC: | 49 | 4BC: | 3B |
| 4BC: | 28 | 1346: | B6 | 492: | 21 | 291: | BC7 | 494: | 3C | 494: | 2D |
| 49A: | A4 | 291: | 9A2 | 1346: | 8A | 1346: | BB | 4A4: | 45 | 291: | B5A |
| 12D6: | 4F6 | 12D6: | 4F0 | 12D6: | 608 | 1346: | 8C | 480: | E4 | 480: | 9E |
| 480: | 62 | 4C3: | 398 | 4C3: | 38C | 4C3: | 318 | 4C3: | 303 | 4C3: | 234 |
| 4C3: | 211 | 4C3: | 199 | 4C3: | 189 | 4C3: | 172 | 4C3: | 104 | 4C3: | DD |
| 4C3: | C6 | 4C3: | E | 4C3: | 788 | 4C3: | 7A6 | 4C3: | 788 | 4C3: | 77F |
| 4C3: | 771 | 4C3: | 75D | 4C3: | 74B | 4C3: | 735 | 4C3: | 727 | 4C3: | 715 |
| 4C3: | 701 | 4C3: | 6F4 | 4C3: | 6E5 | 4C3: | 6C2 | 4C3: | 6BA | 4C3: | 667 |
| 4C3: | 634 | 4C3: | 5E7 | 4C3: | 5B7 | 4C3: | 56D | 4C3: | 54D | 4C3: | 50E |
| 4C3: | 500 | 4C3: | 4EC | 4C3: | 4CA | 4C3: | 4AC | 4C3: | 4B2 | 4C3: | 44A |
| 4C3: | 436 | 4C3: | 426 | 4C3: | 417 | 4C3: | 3EE | 4C3: | B40 | 1346: | 90 |
| 1346: | 96 | 1346: | 94 | 568: | F9 | 568: | AE | 1346: | 9A | 1346: | 98 |
| 57F: | 15F | 57F: | 14C | 57F: | 138 | 57F: | 118 | 57F: | 106 | 57F: | EF |
| 57F: | BB | 57F: | BA | 57F: | 65 | 57F: | 3D | 57F: | 6 | 1346: | 9C |
| 597: | 3AF | 597: | 3AA | 597: | 37F | 597: | 344 | 597: | 319 | 597: | 2D3 |
| 597: | 2CC | 597: | 2BC | 597: | 25D | 597: | 209 | 597: | 1F8 | 597: | 1E5 |
| 597: | 62 | 597: | 11 | 597: | 7BE | 597: | 75C | 597: | 747 | 597: | 724 |
| 597: | 71E | 597: | 704 | 597: | 6EA | 597: | 6CF | 597: | 69F | 597: | 68A |
| 597: | 682 | 597: | 643 | 597: | 632 | 597: | 609 | 597: | 5E7 | 597: | 5DF |
| 597: | 5A2 | 597: | 591 | 597: | 589 | 597: | 542 | 597: | 529 | 597: | 50A |
| 597: | 496 | 597: | 47C | 597: | 475 | 597: | 451 | 597: | 436 | 597: | 3F6 |
| 597: | 7E0 | 597: | 7CE | 597: | 7A7 | 597: | 7A1 | 1346: | 9E | 617: | 64 |
| 617: | 13 | 620: | 2D | 291: | C86 | 291: | CCF | 291: | E02 | 1346: | A0 |
| 625: | 48 | 625: | 1C | 1346: | A2 | 291: | 1081 | 291: | 11AC | 291: | 11FE |
| 291: | 129F | | | | | | | | | | |

What is claimed is:

1. An apparatus for comparing a degree of similarity of two substances comprising:
   means for injecting the two substances into a chromatography column;
   means for converting concentrations of various components in effluent streams of the two substances into chromatograms and then into two histograms, one for each substance;
   means for performing a cross-correlation on the two histograms and calculating 0th, 1st, 2nd and 3rd moments of a cross-correlation function; and
   means for displaying a ratio of the 3rd moment to the 2nd moment.

2. An apparatus for comparing a degree of similarity of an unknown substance to a group of substances comprising:
   (1) means for injecting the unknown substance into a chromatography column and converting concentrations of various components in an effluent stream of the substance into a chromatogram and then into a histogram;
   (2) means for performing a cross-correlation on the histogram of the injected substance and the histogram, previously prepared, for one of the substances in the group of substances and calculating 0th, 1st, 2nd and 3rd moments of a cross-correlation function;
(3) means for displaying a ratio of the 3rd moment to the 2nd moment calculated in step 2; and
(4) means for repeating steps 2 and 3 for each substance in the group of substances.

3. An apparatus for comparing chromatograms comprising:
means for detecting components in an effluent stream of a chromatography column for two samples injected separately into said chromatography column and generating a signal indicative of a concentration of each component in the effluent stream as each sample is injected into said column;
means for converting said signals to two chromatograms;
means for performing a cross-correlation on the two chromatograms;
means for calculating 0th, 1st, 2nd and 3rd moments of a cross-correlation function; and
means for calculating a ratio of said 3rd moment to said 2nd moment and displaying said ratio.

4. The apparatus of claim 3 wherein said means for converting the signals into chromatograms includes means for converting the chromatograms into histograms with one bar for each peak in the chromatogram, with each bar having a height representing an area under the corresponding peak, and wherein the means for performing cross-correlation performs the cross-correlation on the chromatograms after they have been converted into histograms.

5. A method of comparing two chemical substances comprising the steps of:
(1) separately injecting a sample of each of the substances to be compared into a chromatography column;
(2) detecting for each sample components in an effluent stream and converting concentration and time of appearance data so gathered into a chromatogram for each sample, thus producing two chromatograms;
(3) performing a cross-correlation between the two chromatograms;
(4) calculating 0th, 1st, 2nd and 3rd moments of a cross-correlation function;
(5) calculating a ratio of the 3rd moment to the 2nd moment and displaying the ratio.

6. The method of claim 5 further comprising the step of converting each chromatogram to a histogram with one bar per peak, with each bar having a height representing an area under the peak prior to performing the cross-correlation function and wherein the step of calculating the cross-correlation function is performed after the chromatograms have been converted to the histograms.

7. The method of claim 6 where all the steps are repeated to compare one unknown chemical substance to a plurality of known chemical substances.

8. The method of claim 7 wherein the steps of generating the histograms for each cross-correlation calculation are modified so that the unknown sample is injected into the chromatography column only once and its histogram is compared by the cross-correlation and moment ratio calculation steps, one at a time, to each of a plurality of histograms, each representing a previously prepared and stored histogram.

9. A method of comparing two substances for chemical similarity comprising the steps of:
(1) reading digital data defining a chromatogram for each of the two substances into a digital computer;
(2) converting the digital data for each chromatogram into a histogram;
(3) calculating a cross-correlation function of the two histograms;
(4) calculating 0th, 1st, 2nd and 3rd moments of the cross-correlation function;
(5) calculating and displaying a ratio of the 3rd moment to the 2nd moment; and
(6) displaying identification data for the two substances.

10. The method of claim 9, wherein steps 1 through 6 are repeated for a plurality of pairs of substances by utilizing stored digital data relating to chromatographs of the pairs of substances.

* * * * *